(12) United States Patent
Chang et al.

(10) Patent No.: US 10,886,014 B2
(45) Date of Patent: Jan. 5, 2021

(54) VITAL-SIGN DETECTING SYSTEM AND METHOD

(71) Applicant: Wistron Corporation, New Taipei (TW)

(72) Inventors: Yao-Tsung Chang, New Taipei (TW); Yin-Yu Chen, New Taipei (TW); Chuan-Yen Kao, New Taipei (TW); Yao-Shun Tseng, New Taipei (TW); Sheng-Lun Chiou, New Taipei (TW)

(73) Assignee: Wistron Corporation, New Taipei (TW)

( * ) Notice: Subject to any disclaimer, the term of this patent is extended or adjusted under 35 U.S.C. 154(b) by 0 days.

(21) Appl. No.: 16/408,340

(22) Filed: May 9, 2019

(65) Prior Publication Data

US 2020/0281506 A1 Sep. 10, 2020

(30) Foreign Application Priority Data

Mar. 5, 2019 (TW) .............................. 108107258 A
Mar. 5, 2019 (TW) .............................. 108107259 A

(51) Int. Cl.
*A61B 5/00* (2006.01)
*G16H 10/65* (2018.01)
(Continued)

(52) U.S. Cl.
CPC ........... *G16H 10/65* (2018.01); *A61B 5/0015* (2013.01); *A61B 5/02055* (2013.01);
(Continued)

(58) Field of Classification Search
CPC .............. G06K 7/10366; A61B 5/7228; A61B 5/0816; A61B 5/6801
(Continued)

(56) References Cited

U.S. PATENT DOCUMENTS 9,395,434 B2\* 7/2016 Mazzaro ................... G01S 7/02
2006/0066449 A1\* 3/2006 Johnson ............... A61B 5/1113
340/539.12
(Continued)

FOREIGN PATENT DOCUMENTS

CN 101472835 A 7/2009
TW 1511701 B 12/2015
(Continued)

OTHER PUBLICATIONS

Extended European Search Report dated Jan. 2, 2020 in related European Application No. 19178096.4.
(Continued)

*Primary Examiner* — Vernal U Brown
(74) *Attorney, Agent, or Firm* — Donald E. Stout; Stout, Uxa & Buyan, LLP

(57) ABSTRACT

A vital-sign detecting system includes radio-frequency (RF) tags disposed on detected subjects respectively, one of the RF tags being turned on and generating an incident RF signal with a predetermined frequency, and the incident RF signal projecting on a corresponding detected subject to generate a corresponding reflected RF signal; and at least one radio-frequency identification (RFID) radar that turns on one of the RF tags, demodulates the reflected RF signal to obtain vital signal of the corresponding detected subject, and identifies the detected subject according to the turned-on RF tag.

17 Claims, 9 Drawing Sheets

(51) Int. Cl.
  *A61B 90/90* (2016.01)
  *A61B 5/0205* (2006.01)
  *A61B 5/0402* (2006.01)
  *A61B 5/117* (2016.01)
  *G06K 7/10* (2006.01)
  *A61B 5/01* (2006.01)
  *A61B 5/024* (2006.01)
  *A61B 5/08* (2006.01)

(52) U.S. Cl.
  CPC ............ *A61B 5/0402* (2013.01); *A61B 5/117* (2013.01); *A61B 5/7228* (2013.01); *A61B 90/90* (2016.02); *G06K 7/10366* (2013.01); *A61B 5/0008* (2013.01); *A61B 5/01* (2013.01); *A61B 5/024* (2013.01); *A61B 5/0816* (2013.01); *A61B 2562/08* (2013.01)

(58) Field of Classification Search
  USPC ........................................................ 340/10.1
  See application file for complete search history.

(56) References Cited

U.S. PATENT DOCUMENTS

| | | | |
|---|---|---|---|
| 2009/0189740 A1* | 7/2009 | Wiesner | G08C 17/02 340/10.3 |
| 2012/0022348 A1 | 1/2012 | Droitcour et al. | |
| 2012/0268308 A1 | 10/2012 | Tuttle | |
| 2013/0336095 A1* | 12/2013 | Seppa | G01L 9/0016 367/137 |
| 2015/0025333 A1* | 1/2015 | Weinstein | A61B 5/02158 600/301 |
| 2017/0296093 A1* | 10/2017 | Ravid | A61B 5/0215 |

FOREIGN PATENT DOCUMENTS

| | | |
|---|---|---|
| WO | WO 2001/050407 A1 | 7/2001 |
| WO | WO 2018/232414 A1 | 12/2018 |

OTHER PUBLICATIONS

Extended European Search Report dated Jan. 2, 2020 in related European Application No. 19178103.8.

Office Action dated Sep. 2, 2019 in corresponding Taiwan Patent Application No. 108107259.

Aditya Singh et al., "Respiratory Monitoring and Clutter Rejection Using a CW Doppler Radar with Passive RF Tags," IEEE Sensors Journal, vol. 12, No. 3, Mar. 2012, pp. 558-565.

Changzhi Li, et al., "A Review on Recent Advances in Doppler Radar Sensors for Noncontact Healthcare Monitoring," IEEE Transactinos on Microwave Theory and Techniques, vol. 61, No. 5, May 2013, pp. 2046-2060.

Office Action dated Mar. 26, 2020 in related Taiwan Application No. 108107258.

\* cited by examiner

VITAL-SIGN DETECTING SYSTEM AND METHOD

CROSS-REFERENCE TO RELATED APPLICATIONS

This application claims priority to Taiwan Patent Application No. 108107258 and No. 108107259, both filed on Mar. 5, 2019, the entire contents of which are each herein expressly incorporated by reference.

BACKGROUND OF THE INVENTION

1. Field of the Invention

The present invention generally relates to vital-sign detection, and more particularly to a vital-sign detecting system and method capable of identifying a detected subject.

2. Description of Related Art

Body temperature (BT), blood pressure (BP), heart rate (HR) and respiratory rate (RR) are four primary vital signs. The detection and measurement of the vital signs may be used to evaluate health condition or provide a clue to illness of a person.

Conventional non-contact vital-sign detecting systems are used to remotely monitor vital signs, such as heart rate or respiratory rate, of a detected subject. Due to high cost of the detecting system, it is commonly used to monitor plural detected subjects. However, signals respectively associated with the detected subjects may cause interference and therefore decrease measurement accuracy. Further, it becomes difficult for the detecting system to identify individual detected subjects or may even misidentify the detected subjects when they are close to each other.

A need has thus arisen to propose a novel vital-sign detecting scheme capable of identifying the detected subject to improve the conventional vital-sign detecting systems.

SUMMARY OF THE INVENTION

In view of the foregoing, it is an object of the embodiment of the present invention to provide a vital-sign detecting system and method that can identify a detected subject and enhance accuracy.

According to one embodiment, a vital-sign detecting system includes radio-frequency (RF) tags and at least one radio-frequency identification (RFID) radar. The RF tags are disposed on detected subjects respectively, one of the RF tags being turned on and generating an incident RF signal with a predetermined frequency, and the incident RF signal projecting on a corresponding detected subject to generate a corresponding reflected RF signal. The RFID radar turns on one of the RF tags, demodulates the reflected RF signal to obtain vital signal of the corresponding detected subject, and identifies the detected subject according to the turned-on RF tag.

DETAILED DESCRIPTION OF THE INVENTION

Figure 1:
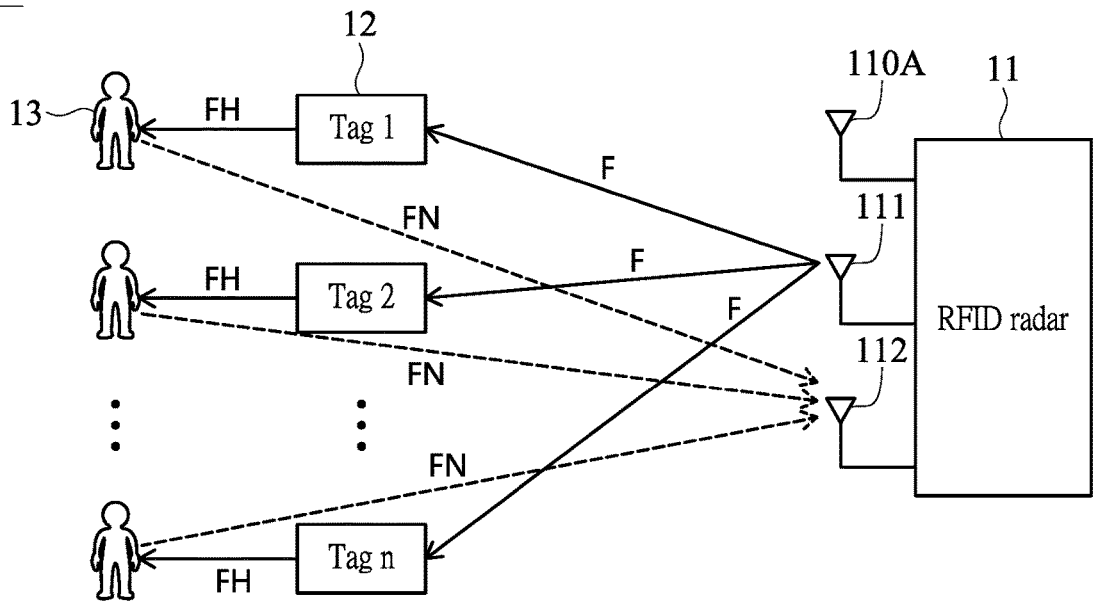
FIG. 1 shows a block diagram illustrating a vital-sign detecting system according to a first embodiment of the present invention.

FIG. 1 shows a block diagram illustrating a vital-sign detecting system 100 (detecting system hereinafter) according to a first embodiment of the present invention. In the embodiment, the detecting system 100 may include a radio-frequency identification (RFID) radar 11 and harmonic radio-frequency (RF) tags 12 (tags hereinafter). The RFID radar 11 may communicate with the tags 12 via an RFID antenna 110A to turn on one of the tags 12. The tags 12 may be disposed on (e.g., worn over chest of) detected subjects 13 respectively.

The RFID radar 11 of the embodiment may transmit an RF signal with a predetermined frequency via a transmitting antenna 111. The tag 12, when turned on, may generate a corresponding incident harmonic signal according to the RF signal. For example, a tag 1 (12), when turned on, receives or senses an RF signal F transmitted via the transmitting antenna 111, and accordingly generates a corresponding incident harmonic signal FH such as second harmonic signal (where FH is twice F in frequency). The incident harmonic signal FH is projected on a detected subject 13 to generate a reflected harmonic signal FN, which is received by the RFID radar 11 via a receiving antenna 112. Body motion of the detected subject 13 may modulate the incident harmonic signal and change phase thereof. Therefore, the RFID radar 11 may obtain vital sign, such as respiratory rate or heart rate, of the detected subject 13 by demodulating the reflected harmonic signal. As only one tag 12 is turned on at a time, the RFID 11 may identify the detected subject 13 corresponding to the received reflected harmonic signal.

Figure 2:
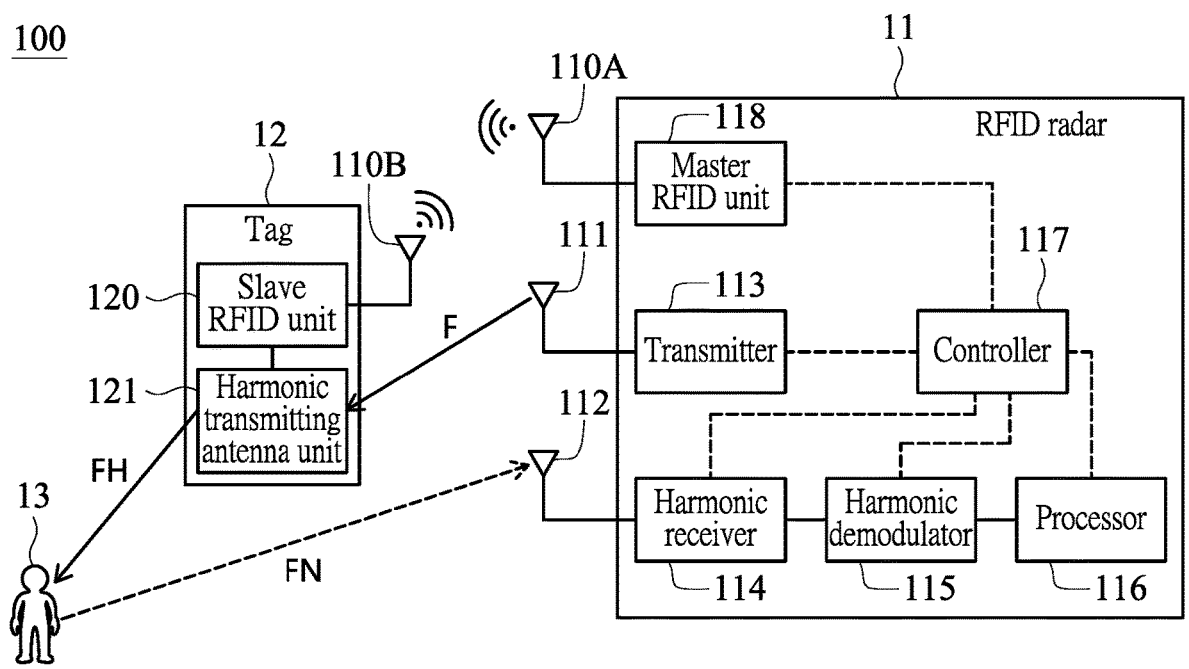
FIG. 2 shows a detailed block diagram of the detecting system of FIG. 1.

FIG. 2 shows a detailed block diagram of the detecting system 100 of FIG. 1. Only one detected subject 13 and the corresponding tag 13 are shown for brevity. In the embodiment, the RFID radar 11 may include a master RFID unit 118, and the tag 12 may include a slave RFID unit 120. The master RFID unit 118 may communicate with the slave RFID unit 120 via an RFID antenna 110A (of the RFID radar 11) and an RFID antenna 110B (of the tag 12) such that only one tag 12 is turned on at a time.

In the embodiment, the RFID radar 11 may include a transmitter 113 configured to generate an RF signal F with a predetermined frequency. The generated RF signal F may be transmitted to the tag 12 via the transmitting antenna 111. The tag 12 may include a harmonic transmitting antenna unit 121 configured to generate resonant reaction as a resonant frequency of the harmonic transmitting antenna unit 121 is the same as the frequency of the RF signal F, thereby generating a corresponding incident harmonic signal FH such as second harmonic signal.

The RFID radar 11 of the embodiment may include a harmonic receiver 114 configured to receive a reflected harmonic signal FN, with frequency being the same as the incident harmonic signal FH but phase demodulated by body motion of the detected subject 13 associated with the turned-on tag 12, via the receiving antenna 112.

The RFID radar 11 of the embodiment may include a harmonic demodulator 115 configured to demodulate the reflected harmonic signal FN (received from the harmonic receiver 114) to obtain a baseband signal containing phase change information. The RFID radar 11 may include a processor 116 including an analog-to-digital converter and a digital signal processor. The processor 116 is configured to perform analog-to-digital conversion on the baseband signal (outputted from the harmonic demodulator 115) and remove high-frequency component, thereby obtaining vital sign, such as respiratory rate or heart rate, of the detected subject 13 through computation. Specifically, high-frequency component may be removed by the digital signal processor, which may, for example, remove unwanted harmonic signal related to respiration, and remove noise. The RFID radar 11 of the embodiment may include a controller 117 configured to control operation of the master RFID unit 118, the transmitter 113, the harmonic receiver 114, the harmonic demodulator 115 and the processor 116. In the embodiment, as shown in FIG. 2, the transmitter 113 is connected to the transmitting antenna 111 to transmit the RF signal F, the harmonic receiver 114 is connected to the receiving antenna 112 to receive the reflected harmonic signal FN, the harmonic demodulator 115 is connected to the harmonic receiver 114 to demodulate the reflected harmonic signal FN, the processor 116 is connected to the harmonic demodulator 115 to process the baseband signal, and the master RFID unit 118 is connected to the RFID antenna 110A for communicating with the RFID antenna 110B of the slave RFID unit 120.

Figure 3A:
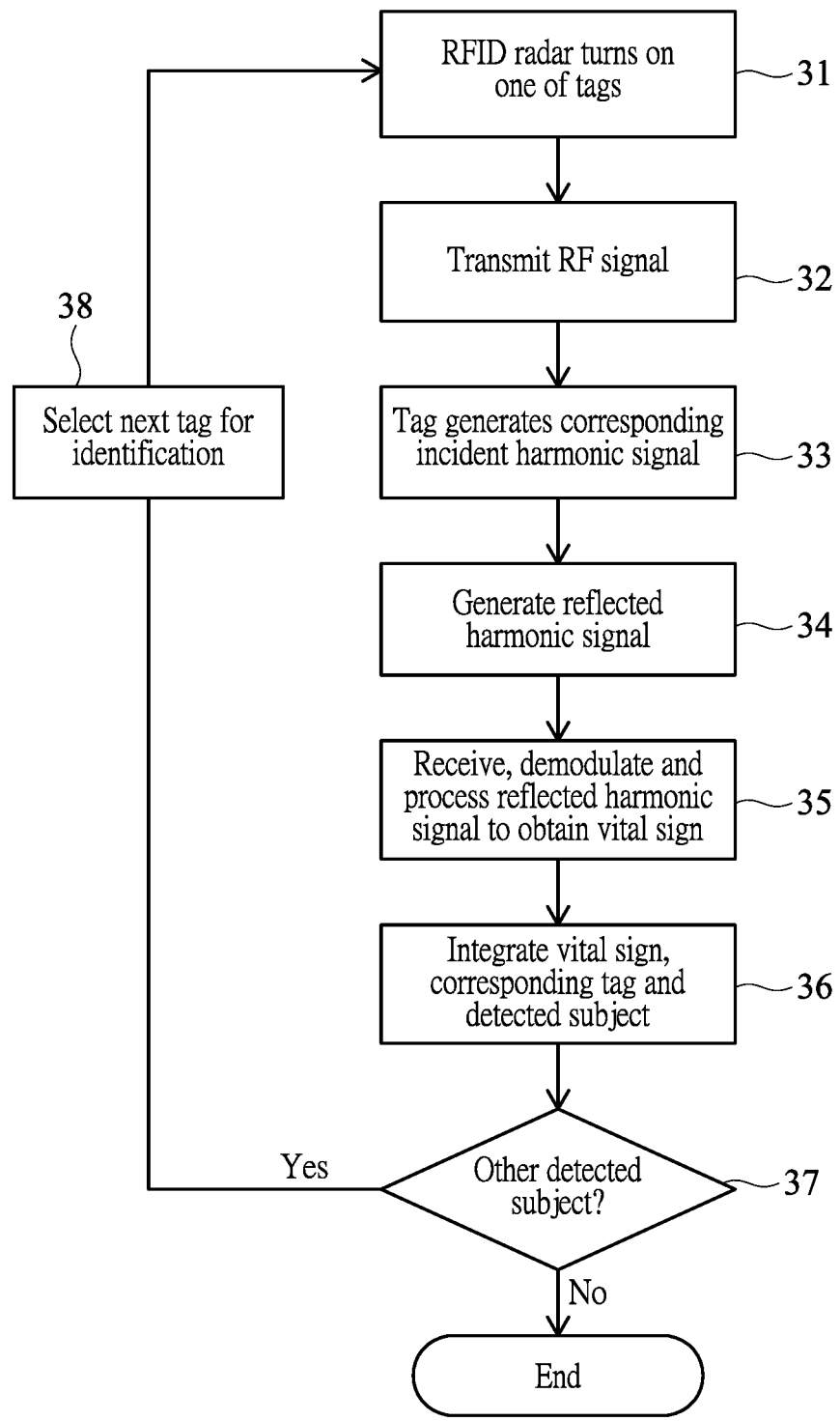
FIG. 3A shows a flow diagram illustrating a vital-sign detecting method according to the first embodiment of the present invention.
Figure 3B:
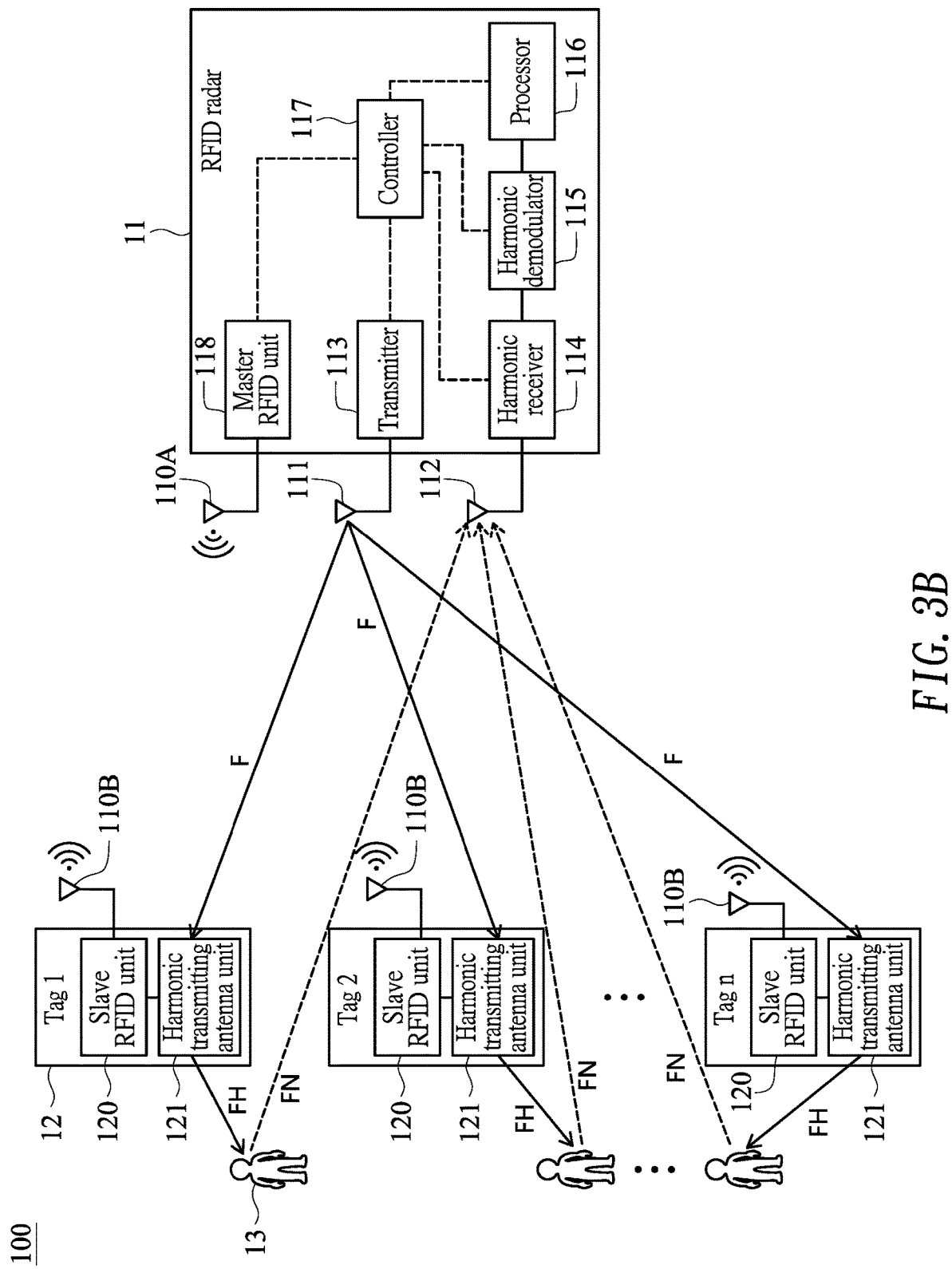
FIG. 3B shows a block diagram illustrating a detecting system associated with FIG. 3A.

FIG. 3A shows a flow diagram illustrating a vital-sign detecting method 300 (detecting method hereinafter) according to the first embodiment of the present invention, and FIG. 3B shows a block diagram illustrating a detecting system 100 associated with FIG. 3A. In step 31, the RFID radar 11 turns on one of the tags 12. In step 32, the transmitter 113 of the RFID radar 11 transmits an RF signal F with a predetermined frequency to the turned-on tag 1 (12) via the transmitting antenna 111. The harmonic transmitting antenna unit 121 of the tag 12 generates resonant reaction with the RF signal F, thereby generating an incident harmonic signal FH to a corresponding detected subject 13 (step 33).

In step 34, body motion of the detected subject 13 associated with the turned-on tag 12 modulates and changes phase of the incident harmonic signal FH, thereby generating a reflected harmonic signal FN. In step 35, the harmonic receiver 114 of the RFID radar 11 receives the reflected harmonic signal FN. Subsequently, the harmonic demodulator 115 of the RFID radar 11 demodulates the reflected harmonic signal FN to obtain a baseband signal containing phase change information. Next, the processor 116 of the RFID radar 11 performs analog-to-digital conversion on the baseband signal and removes high-frequency component, thereby obtaining vital sign, such as respiratory rate or heart rate, of the detected subject 13 through computation.

In step 36, the vital sign, the corresponding tag 12 and the detected subject 13 are integrated. The turned-on tag 12 may be used as identification (ID) for identifying the detected subject 13.

Next, if there is still detected subject 13 to be detected (step 37), the RFID radar 11 selects next tag for identification (step 38), and steps 31-36 are performed again. That is, the selected tag 12 is turned on (step 31), an RF signal F with a predetermined frequency is transmitted to the turned-on tag 12 (step 32), an incident harmonic signal FH is generated to a corresponding detected subject 13 (step 33), a reflected harmonic signal FN is generated (step 34), vital sign of the detected subject 13 is obtained (step 35), and the vital sign, the corresponding tag 12 and the detected subject 13 are integrated (step 36). If no detected subject 13 is left to be detected in step 37, the flow of the detecting method 300 stops.

Figure 4:
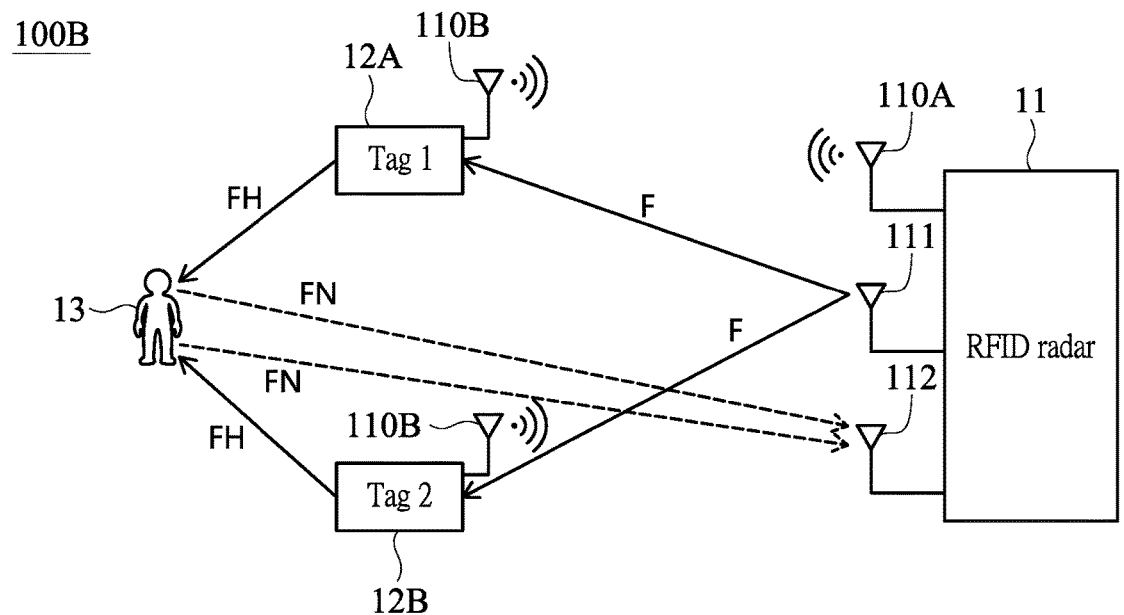
FIG. 4 shows a block diagram illustrating a detecting system according to a first modified embodiment of the first embodiment of the present invention.

FIG. 4 shows a block diagram illustrating a detecting system 100B according to a first modified embodiment of the first embodiment of the present invention. Compared to the detecting system 100 of FIG. 3B, the present embodiment (FIG. 4) adopts more than one of the tags 12 (e.g., tags 12A and 12B) disposed on a single detected subject 13. Accordingly, the RFID radar 11 may detect plural vital signs of a single detected subject 13.

Figure 5:
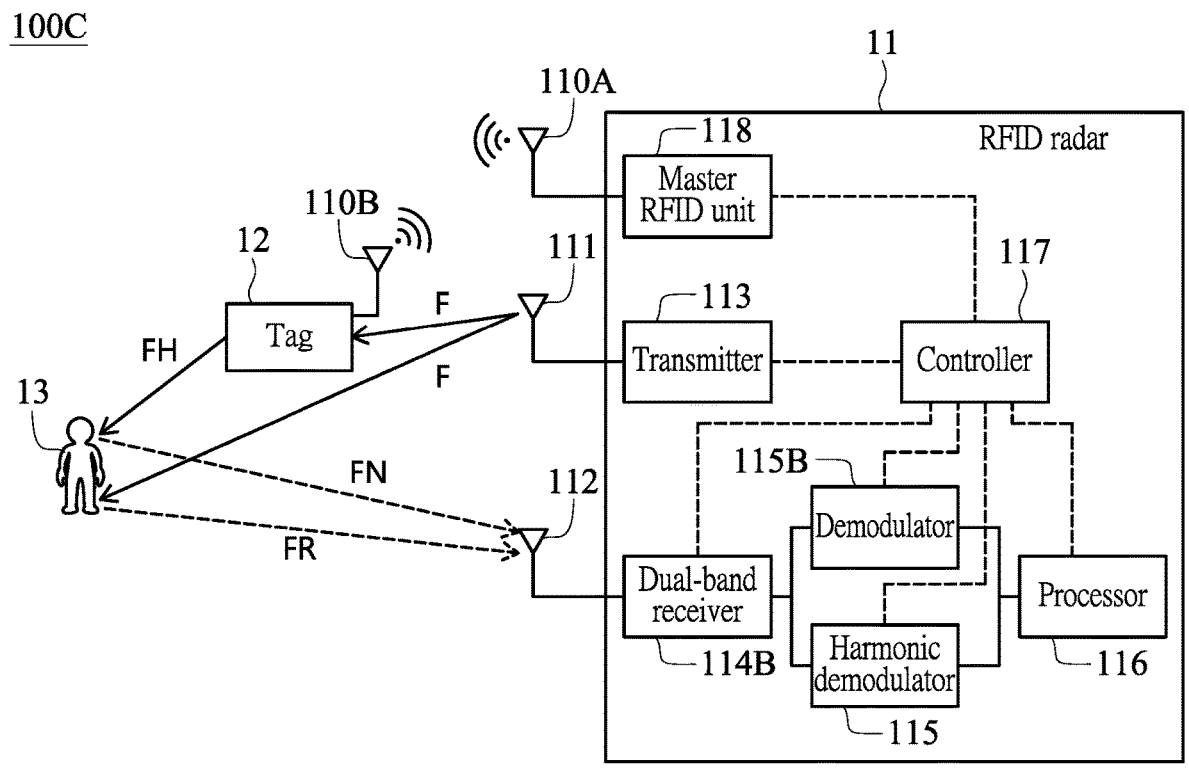
FIG. 5 shows a block diagram illustrating a detecting system according to a second modified embodiment of the first embodiment of the present invention.

FIG. 5 shows a block diagram illustrating a detecting system 100C according to a second modified embodiment of the first embodiment of the present invention. Compared to the detecting system 100 of FIG. 2, the RFID radar 11 of the present embodiment (FIG. 5) adopts a dual-band receiver 114B instead of the harmonic receiver 114. One band of the dual-band receiver 114B is similar to that in FIG. 2 for receiving the reflected harmonic signal FN, and the other band of the dual-band receiver 114B is used to receive a reflected RF signal FR reflected from the detected subject 13 (but not via tag 12) who is projected with the RF signal F. The received reflected RF signal FR is demodulated by a demodulator 115B. Accordingly, the RFID radar 11 may detect plural vital signs of a single detected subject 13 by time division multiplexing within the same period.

Figure 6:
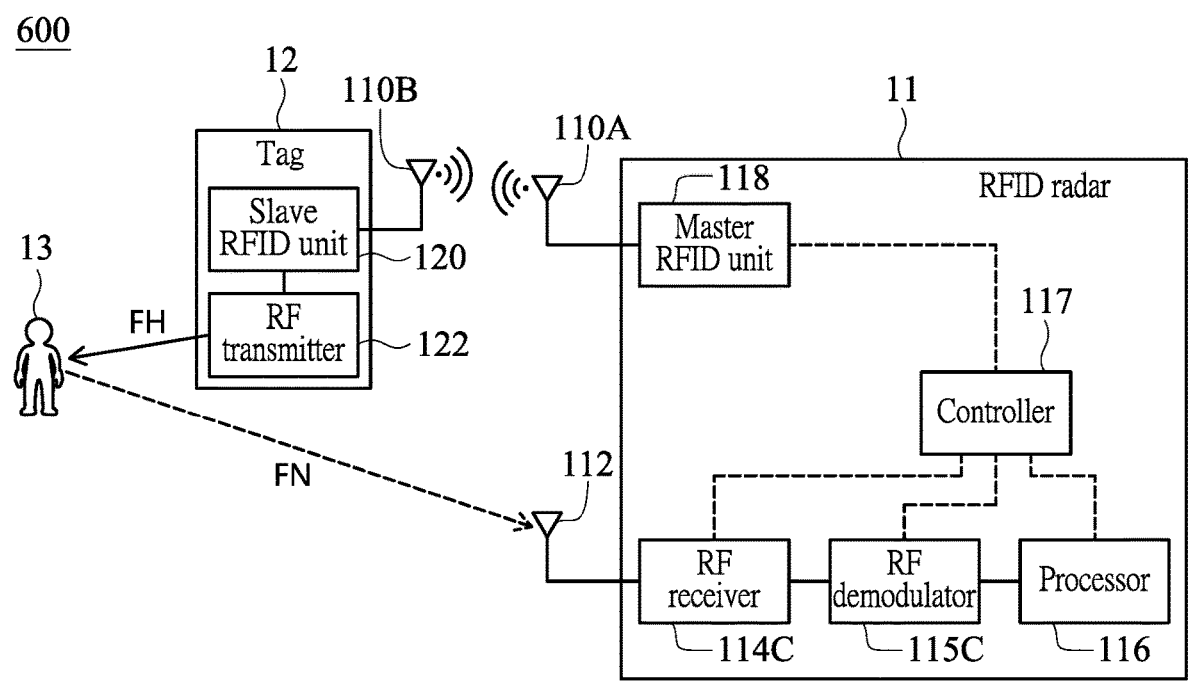
FIG. 6 shows a block diagram illustrating a vital-sign detecting system according to a second embodiment of the present invention.

FIG. 6 shows a block diagram illustrating a vital-sign detecting system 600 (detecting system hereinafter) according to a second embodiment of the present invention. The second embodiment is similar to the first embodiment with the exceptions as described below.

In the embodiment, the RF tag 12 (tag hereinafter) may include an RF transmitter 122 configured to transmit an incident RF signal FH with a predetermined frequency when the tag 12 is turned on. The RFID radar 11 of the embodiment may include an RF receiver 114C, which is similar to the harmonic receiver 114 in the first embodiment, for receiving a reflected RF signal FN. The RFID radar 11 of the embodiment may include RF demodulator 115C, which is similar to the harmonic demodulator 115 in the first embodiment, for demodulating the reflected RF signal FN (received by the RF receiver 114C) to obtain a baseband signal containing phase change information.

The incident RF signal FH may be projected on the detected subject 13 to generate a corresponding reflected RF signal FN, which may be received by the receiving antenna 112 of the RFID radar 11. Body motion of the detected subject 13 associated with the turned-on tag 12 may modulate the incident RF signal FH and change phase thereof. Therefore, the RFID radar 11 may obtain vital sign, such as respiratory rate or heart rate, of the detected subject 13 by demodulating the reflected RF signal FN. The RFID radar 11 of the embodiment does not require the transmitter 113 and the transmitting antenna 111 as in the first embodiment.

Figure 7A:
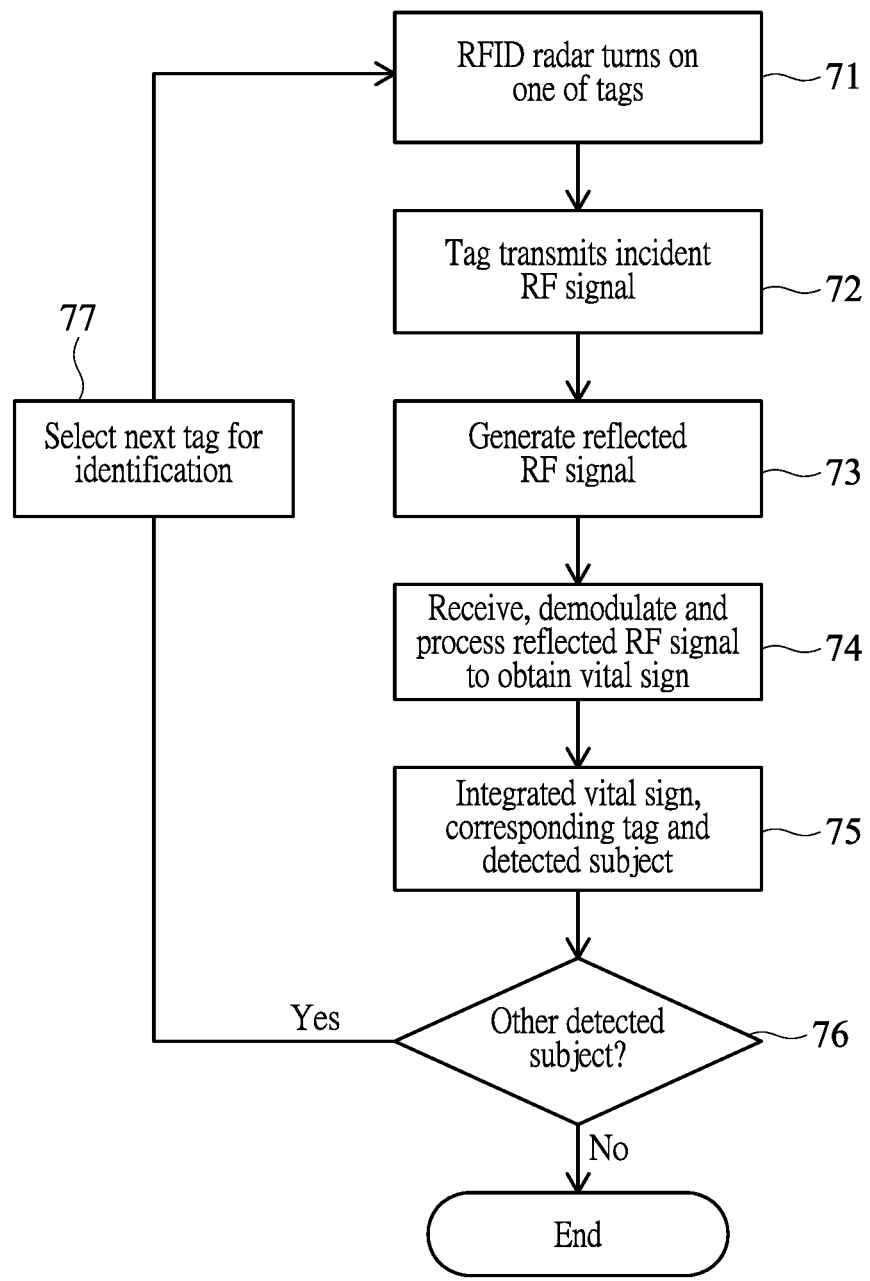
FIG. 7A shows a flow diagram illustrating a vital-sign detecting method according to the second embodiment of the present invention.
Figure 7B:
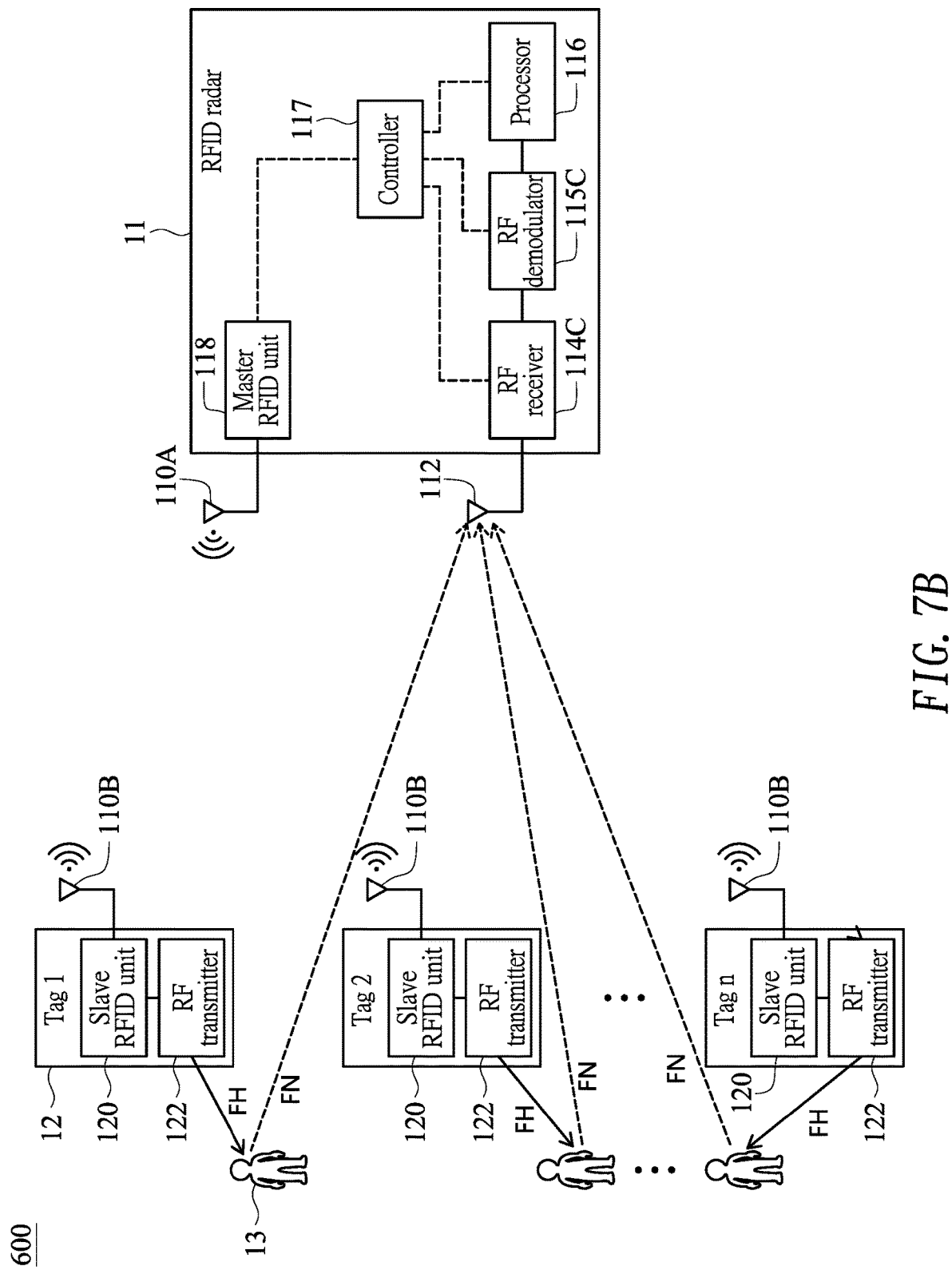
FIG. 7B shows a block diagram illustrating a detecting system associated with FIG. 7A.

FIG. 7A shows a flow diagram illustrating a vital-sign detecting method 700 (detecting method hereinafter) according to the second embodiment of the present invention, and FIG. 7B shows a block diagram illustrating a detecting system 600 associated with FIG. 7A. In step 71, the RFID radar 11 turns on one of the tags 12. In step 72, the RF transmitter 122 of the turned-on tag 12 transmits incident RF signals FH with a predetermined frequency.

In step 73, body motion of the detected subject 13 associated with the turned-on tag 12 modulates the incident RF signal FH and changes phase thereof, thereby generating a reflected RF signal FN. In step 74, the RF receiver 114C of the RFID radar 11 receives the reflected RF signal FN. The RF demodulator 115C of the RFID radar 11 demodulates the reflected RF signal FN to obtain a baseband signal containing phase change information. The processor 116 of the RFID radar 11 performs analog-to-digital conversion on the phase baseband signal and removes high-frequency component, thereby obtaining vital sign, such as respiratory rate or heart rate, of the detected subject 13 through computation.

In step 75, the vital sign, the corresponding tag 12 and the detected subject 13 are integrated. The turned-on tag 12 may be used as identification (ID) for identifying the detected subject 13.

Next, if there is still detected subject 13 to be detected (step 76), the RFID radar 11 selects next tag 12 for identification (step 77), and steps 71-75 are performed again. If no detected subject 13 is left to be detected in step 76, the flow of the detecting method 700 stops.

Figure 8:
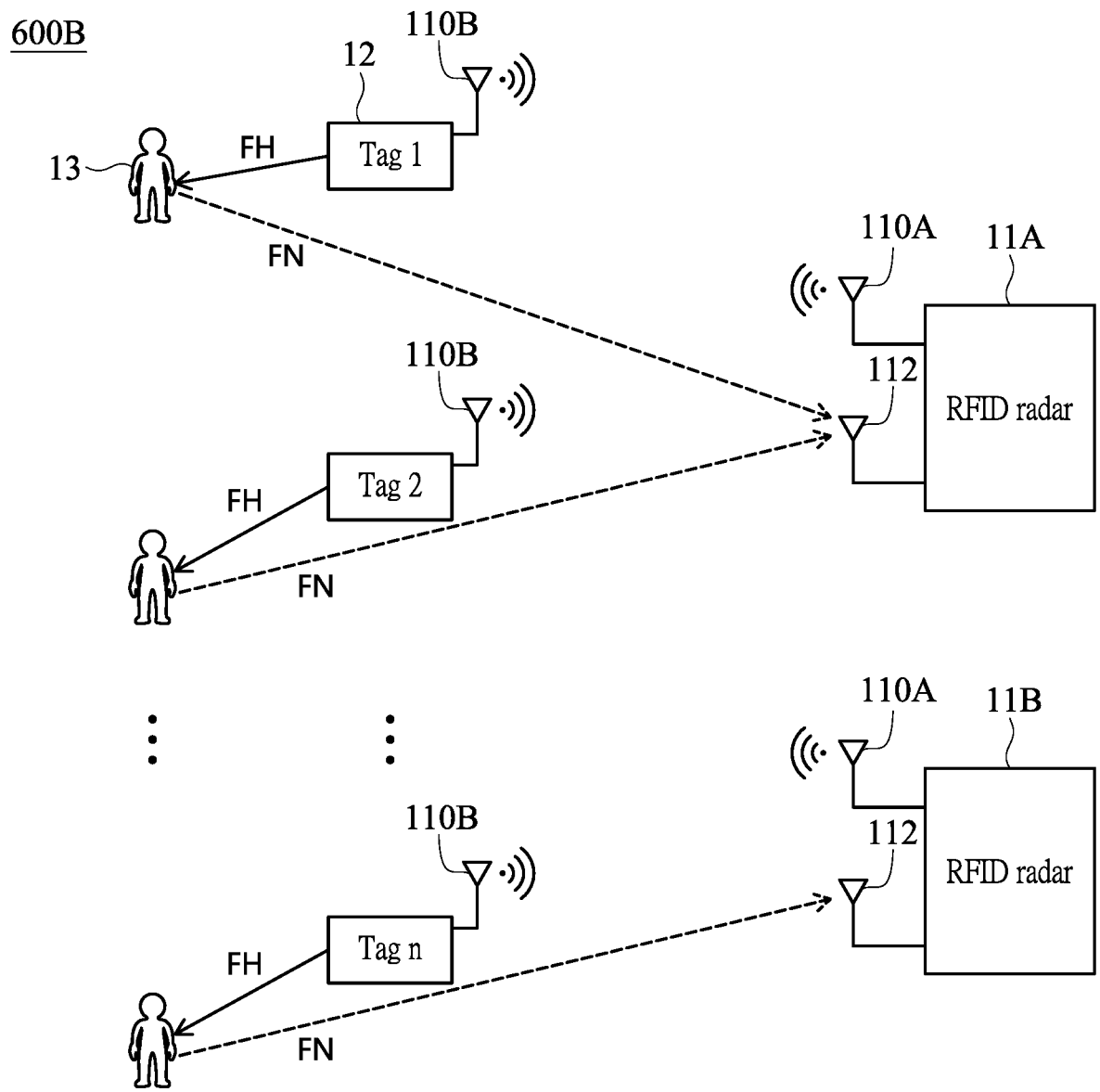
FIG. 8 shows a block diagram illustrating a detecting system according to a first modified embodiment of the second embodiment of the present invention.

FIG. 8 shows a block diagram illustrating a detecting system 600B according to a first modified embodiment of the second embodiment of the present invention. Compared to the detecting system 600 of FIG. 7B, the present embodiment (FIG. 8) adopts plural (e.g., two) RFID radars 11A land 11B corresponding to different tags 12 and detected subjects 13 respectively. Accordingly, the RFID radars 11A and 11B may perform plural identifications at the same time, while the second embodiment (FIG. 7B) may only perform single identification at a time.

Figure 9:
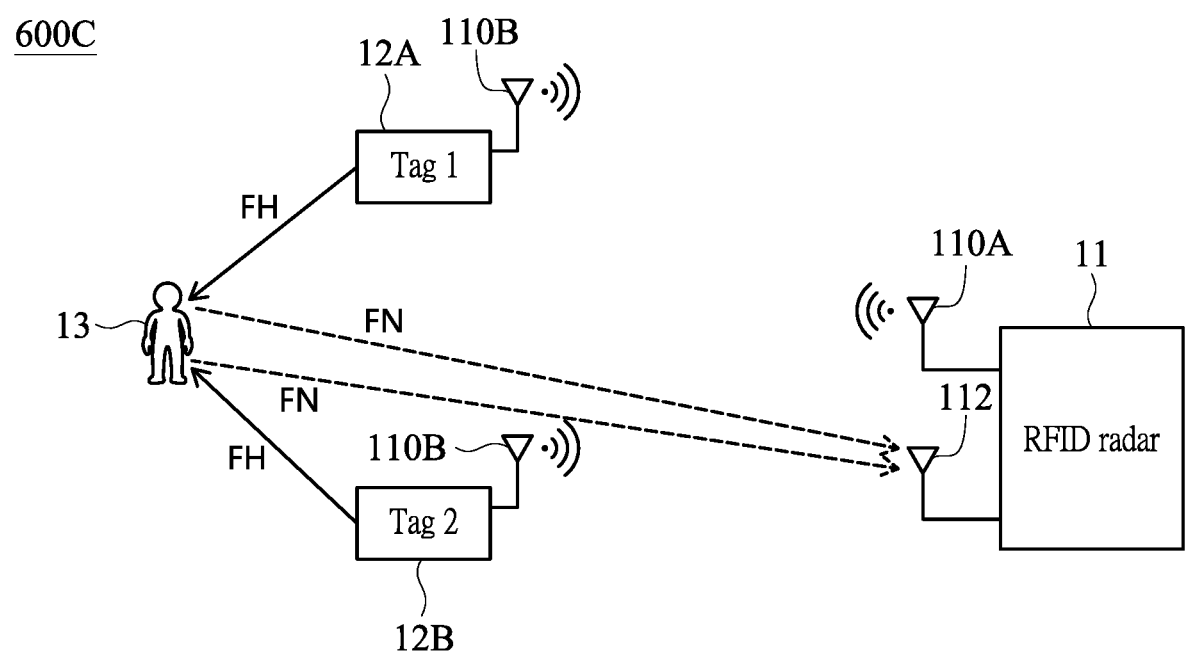
FIG. 9 shows a block diagram illustrating a detecting system according to a second modified embodiment of the second embodiment of the present invention.

FIG. 9 shows a block diagram illustrating a detecting system 600C according to a second modified embodiment of the second embodiment of the present invention. Compared to the detecting system 600 of FIG. 6, the present embodiment (FIG. 9) adopts more than one of the tags 12 (e.g., tags 12A and 12B) disposed on a single detected subject 13. Accordingly, the RFID radar 11 may detect plural vital signs of a single detected subject 13.

Although specific embodiments have been illustrated and described, it will be appreciated by those skilled in the art that various modifications may be made without departing from the scope of the present invention, which is intended to be limited solely by the appended claims.

What is claimed is:

1. A vital-sign detecting system, comprising:
    at least one radio-frequency identification (RFID) radar that transmits a radio-frequency (RF) signal with a predetermined frequency; and
    a plurality of harmonic RF tags disposed on detected subjects respectively, one of the harmonic RF tags being turned on by the RFID radar and generating an incident harmonic signal according to the RF signal, the incident harmonic signal projecting on a corresponding detected subject to generate a corresponding reflected harmonic signal;
    wherein the RFID radar is external to the harmonic RF tags, and the incident harmonic signal generated by the harmonic RF tag is a harmonic signal of the RF signal transmitted to the harmonic RF tag by the RFID radar;
    wherein the RFID radar demodulates the reflected harmonic signal to obtain vital sign of the corresponding detected subject, and identifies the detected subject according to the turned-on harmonic RF tag.

2. The system of claim 1, wherein the RFID radar comprises a master RFID unit and the harmonic RF tag comprises a slave RFID unit, the master RFID unit communicating with the slave RFID unit to turn on the corresponding harmonic RF tag.

3. The system of claim 1, wherein the RFID radar comprises:
    a transmitter that generates the RF signal;
    a harmonic receiver that receives the reflected harmonic signal; and
    a harmonic demodulator that demodulates the reflected harmonic signal to obtain a baseband signal.

4. The system of claim 3, wherein the harmonic receiver comprises a dual-band receiver, one band of which is used to receive the reflected harmonic signal, and another band of which is used to receive a reflected RF signal directly reflected from the detected subject.

5. The system of claim 3, wherein the RFID radar further comprises:
    a processor that performs analog-to-digital conversion on the baseband signal and remove high-frequency component thereof, thereby obtaining vital sign of the detected subject through computation.

6. The system of claim 1, wherein the harmonic RF tag comprises:
    a harmonic transmitting antenna unit that generates resonant reaction when a resonant frequency of the harmonic transmitting antenna unit is the same as the frequency of the RF signal, thereby generating the corresponding incident harmonic signal.

7. The system of claim 1, wherein more than one of the harmonic RF tags are disposed on at least one of the detected subjects.

8. A vital-sign detecting system, comprising:
    a plurality of radio-frequency (RF) tags disposed on detected subjects respectively, one of the RF tags being turned on and generating an incident RF signal with a predetermined frequency, and the incident RF signal projecting on a corresponding detected subject to generate a corresponding reflected RF signal; and
    at least one radio-frequency identification (RFID) radar that turns on one of the RF tags, demodulates the reflected RF signal to obtain a vital sign of the corresponding detected subject, and identifies the detected subject according to the turned-on RF tag, the RFID radar being external to the RF tags.

9. The system of claim 8, wherein the RFID radar comprises a master RFID unit and the RF tag comprises a slave RFID unit, the master RFID unit communicating with the slave RFID unit to turn on the corresponding RF tag.

10. The system of claim 8, wherein the RFID radar comprises:
    an RF receiver that receives the reflected RF signal; and
    an RF demodulator that demodulates the reflected RF signal to obtain a baseband signal.

11. The system of claim 10, wherein the RFID radar further comprises:

a processor that performs analog-to-digital conversion on the baseband signal and remove high-frequency component thereof, thereby obtaining vital sign of the detected subject through computation.

12. The system of claim 8, wherein said at least one RFID radar comprises a plurality of RF demodulators for demodulating the reflected RF signals with the predetermined frequency.

13. The system of claim 8, wherein more than one of the RF tags are disposed on at least one of the detected subjects.

14. A vital-sign detecting method, comprising:

a radio-frequency identification (RFID) radar performing radio-frequency identification (RFID) communication to turn on one of a plurality of radio-frequency (RF) tags, which are disposed on detected subjects respectively;

generating an incident RF signal with a predetermined frequency;

projecting the incident RF signal on a corresponding detected subject to generate a corresponding reflected RF signal;

the RFID radar demodulating the reflected RF signal to obtain vital sign of the corresponding detected subject; and identifying the detected subject according to the turned-on RF tag;

wherein the RFID radar is external to the RF tags, and the incident RF signal generated by the RF tag is a harmonic signal of an RF signal transmitted to the RF tag by the RFID radar.

15. The method of claim 14, wherein the incident RF signal is generated by resonant reaction.

16. The method of claim 14, wherein the reflected RF signal is demodulated to obtain a baseband signal.

17. The method of claim 16, further comprising:

performing analog-to-digital conversion on the baseband signal and removing high-frequency component thereof, thereby obtaining vital sign of the detected subject through computation.

* * * * *